United States Patent [19]

Bell et al.

[11] Patent Number: 5,013,329

[45] Date of Patent: May 7, 1991

[54] CONVERSION OF LIGHT HYDROCARBONS TO ETHER RICH GASOLINE

[75] Inventors: Weldon K. Bell, Pennington; Werner O. Haag; Mohsen N. Harandi, both of Lawrenceville; Hartley Owen, Belle Mead, all of N.J.

[73] Assignee: Mobil Oil Corporation, New York, N.Y.

[21] Appl. No.: 331,201

[22] Filed: Mar. 31, 1989

[51] Int. Cl.⁵ .................................................. C10L 1/18
[52] U.S. Cl. .................................... 44/448; 44/449; 568/697
[58] Field of Search ............... 44/53, 56, 77; 568/697; 585/331

[56] References Cited

U.S. PATENT DOCUMENTS

| | | | |
|---|---|---|---|
| 3,849,082 | 11/1974 | Kozlowski et al. | 44/56 |
| 3,912,463 | 10/1975 | Kozlowski et al. | 44/56 |
| 4,423,251 | 12/1983 | Pujado et al. | 568/697 |
| 4,503,264 | 3/1985 | Al-Muddarris | 568/697 |
| 4,506,106 | 3/1985 | Hsia et al. | 585/312 |
| 4,647,703 | 3/1987 | Torck et al. | 568/697 |
| 4,684,757 | 8/1987 | Avidan et al. | 585/331 |
| 4,714,787 | 12/1987 | Bell et al. | 568/697 |

*Primary Examiner*—Margaret B. Medley
*Attorney, Agent, or Firm*—Alexander J. McKillop; Charles J. Speciale; L. G. Wise

[57] ABSTRACT

A process is disclosed for converting a light hydrocarbon feedstock that contains a mixture of linear and branched olefins to ether-rich high octane gasoline streams that include tertiary alkyl and isoalkyl ethers such as MTBE, TAME, methyl isopropyl ether (MIPE), and methyl sec-butylether (MSBE). The conversion is achieved by utilizing the differing reactivity of tertiary olefins under selected conditions compared to linear olefins in the catalyzed etherification processes. The discovery has been made that unreacted olefins from the etherification reactions can be converted to gasoline boiling range hydrocarbons by contacting them with zeolite catalyst at elevated temperature. Further, it has been discovered that unreacted paraffins in the integrated process can be dehydrogenated to produce $C_3$–$C_4$ olefins which can be recycled to the etherification process.

22 Claims, 2 Drawing Sheets

CONVERSION OF LIGHT HYDROCARBONS TO ETHER RICH GASOLINE

This invention relates to a process for the conversion of light hydrocarbons to gasoline rich in tertiary alkyl ethers and isoalkyl ethers. More particularly, the invention relates to an integrated process for the conversion of a hydrocarbon feedstream containing light linear and branched olefins to ether and the serial conversion of unreacted olefins to gasoline boiling range hydrocarbons. The invention, more specifically, pertains to the manufacture of gasoline containing methyl tertiary butyl ether (MTBE) and tertiary amyl methyl ether (TAME) plus lower isoalkyl ethers.

BACKGROUND OF THE INVENTION

One of the more important recent developments in the petroleum refining arts is the establishment in the prior art of new processes to produce high octane gasolines blended with lower aliphatic alkyl ethers as octane boosters and supplementary fuels. $C_5$–$C_7$ methyl alkyl ethers, especially methyl tertiary butyl ether (MTBE) and tertiary amyl methyl ether (TAME) have been found particularly useful for enhancing gasoline octane. Therefore, improvements to the processes related to the production of these and similar ethers in the course of gasoline production are matters of high importance and substantial challenge to research workers in those arts.

It is known that alkyl tert-alkyl ethers can be prepared by reacting a primary alcohol with an olefin having a double bond on a tertiary carbon atom, thus methanol reacts with isobutylene and isopentenes (2 methyl 1-butene or 2 methyl 2-butene) to form respectively methyl tert-butyl ether (MTBE) and methyl tert-amyl ether (TAME). The reaction is selective for tertiary olefins so that it constitutes a valid process for their removal from olefinic streams in which they are contained together with linear unreactive olefins. The reaction has an equilibrium which is favorable to the synthesis of the ether as the reaction temperature is lowered, in accordance with the reactions negative enthalpy.

It is known that the reaction is catalyzed by Lewis acids (aluminum trichloride, boron trifluoride), mineral acids (sulfuric acid) and organic acids (alkyl and aryl sulfonic acids, ion exchange resins). Particularly suitable for the task are ion exchange resins in their acid form and it is known that the best results are obtained by means of macroreticular resins of the type "Amberlyst 15". By means of such last named catalysts it is possible to reach thermodynamic equilibrium within industrially acceptable contact times in the temperature range of 50°–60° C.

U.S. Pat. No. 4,262,145 to Selwitz et al. discloses the catalytic reaction of a branched olefin such as isobutylene, 2-methylpentene-2, 2-methylbutene-2, and 2,3-dimethyloctene-2 with a lower alkanol such as methanol to form a mixed ether such as methyl tert-butyl ether. The catalyst disclosed is silicotungstic acid.

A process is also known for manufacturing ethers from linear mono-olefins, thereby augmenting the supply of highoctane blending stock for gasoline. The lower molecular weight ethers, such as methyl isopropyl ether, are in the gasoline boiling range and are known to have a high blending octane number. U.S. Pat. No. 4,714,787 to Bell et al., incorporated herein by reference in its entirety, provides a catalytic process for selectively reacting one or more linear mono-olefins with a primary or secondary lower molecular weight alcohol to form the corresponding ether. The active acidic catalyst component for the process is selected from the group consisting of sulfonated ion-exchange resins and crystalline silicates having a pore size greater than 5 angstrom units. Of the crystalline silicates, those preferred include crystalline zeolites having a silica to alumina mol ratio greater than about 12. In a particularly preferred embodiment, methanol and propylene are reacted to selectively form methyl isopropyl ether (MIPE).

A preferred feedstock for the manufacture of MTBE and TAME in petroleum refinery operations is the light hydrocarbon stream from FCC operations. These streams are rich in $C_4$+tertiary olefins such as isobutylene. However, they also contain significant amounts of linear olefins plus linear and branched paraffins. The linear olefins, particularly propylene and n-butene, are not etherified in the prior art MTBE processes. Conventionally, these linear unreacted olefins are carried through the process and separated downstream. In this regard they represent a burden on the volumetric effectiveness of the etherification process, providing no assistance to the production of ether-rich high octane gasoline.

Processes for the conversion of olefins as well as oxygenates to gasoline are well-known in the prior art. The processes for the conversion of methanol to olefins and olefins to gasoline are but representative of a series of analogous processes based upon the catalytic capabilities of zeolites. It is known that zeolites, such as ZSM-5, can convert methanol to hydrocarbons of higher average molecular weight. Depending on various conditions of space velocity, temperature and pressure methanol, and lower oxygenates in general, can be converted in the presence of zeolite type catalyst to olefins which may then oligomerize to provide gasoline or distillate or may be converted further to produce aromatics.

The feasibility and adaptability of the basic chemistry of zeolite oxygenates conversion to produce useful conversion processes has been the subject of much inventive research activity. Recent developments in zeolite catalyst and hydrocarbon conversion processes have created interest in using oxygenates and olefinic and paraffinic feedstocks for producing $C_5$+ gasoline, diesel fuel, aromatics, etc. In addition to the basic work derived from ZSM-5 type zeolite catalyst, a number of discoveries have contributed to the development of a new industrial process. This process has significance as a safe, environmentally acceptable technique for utilizing feedstocks that contain lower olefins, especially $C_2$–$C_5$ alkenes. In U.S. Pat. Nos. 3,960,978 and 4,021,502, Plank, Rosinski and Givens disclose conversion of $C_2$–$C_5$ olefins, alone or in admixture with paraffinic components into higher hydrocarbons over crystalline zeolites having controlled acidity. Reaction conditions of moderate severity favor the conversion of olefins to predominantly gasoline boiling range products with little paraffins conversion. Milder reaction temperatures and high operating pressures can produce distillate range fuels as well from lower olefins. Garwood et al. have also contributed improved processing techniques in U.S. Pat. Nos. 4,150,062, 4,211,640 and 4,227,992. The above identified disclosures are incorporated herein by reference.

Accordingly, it is an object of the present invention to provide a process for the enhanced conversion of olefinic components of hydrocarbon streams containing mixed branched and linear olefins to ether-rich high octane gasoline.

It is another object of the present invention to provide an integrated process for the sequential conversion of tertiary olefins and linear olefins to lower alkyl ethers and the conversion of unreacted olefins to gasoline.

Yet another object of the instant invention is to provide an integrated process for converting light hydrocarbons comprising mixed olefins plus paraffins to high octane ethers and gasoline.

SUMMARY OF THE INVENTION

A process has been discovered for converting a light hydrocarbon feedstock that contains a mixture of linear and branched olefins to ether-rich high octane gasoline streams that include tertiary alkyl and isoalkyl ethers such as MTBE, TAME, methyl isopropyl ether (MIPE), and methyl sec-butyl ether (MSBE). The conversion is achieved by utilizing the differing reactivity of tertiary olefins under selected conditions compared to linear olefins in the catalyzed etherification processes. The discovery has been made that unreacted olefins from the etherification reactions can be converted to higher molecular weight products comprising gasoline, distillate or aromatics by contacting them with zeolite catalyst at elevated temperature, employing either the Mobil Olefins to Gasoline (MOG), Mobil Olefins to Gasoline and Distillate (MOGD) or aromatics forming M-2 Forming Mobil processes. Further, it has been discovered that unreacted paraffins in the integrated process can be dehydrogenated to produce $C_3-C_4$ olefins which can be recycled to the etherification process.

More particularly, an integrated process has been discovered for the production of ether-rich liquid fuels which comprises: contacting a fresh mixture of excess lower alkanol and a light hydrocarbon feedstock containing linear olefins and $C_4+$ tertiary olefins with an acidic etherification catalyst in a first etherification zone under tertiary olefin etherification conditions whereby an etherification effluent stream containing lower alkyl tertiary alkyl ethers is produced. Separating the etherification effluent stream to provide a first stream comprising ether-rich $C_5+$ gasoline and a second stream comprising unreacted methanol and linear olefins of $C_5-$ hydrocarbons. The second stream is contacted with an acidic catalyst in a second etherification zone under conditions effective to etherify said linear olefinic hydrocarbons. A first stream is recovered form the second etherification zone comprising $C_5+$ gasoline containing lower alkyl ethers of said $C_5-$ linear olefins and a second stream comprising unreacted olefins of $C_4-$ hydrocarbons from said second etherification zone. The second stream is passed to an olefins conversion zone in contact with an acidic metallosilicate catalyst under olefins and oxygenates conversion conditions at elevated temperature whereby higher molecular weight liquid fuels are produced. Paraffins in the effluent from the olefins conversion zone can be separated and dehydrogenated to produce olefins which can be recycled to the first etherification zone.

DETAILED DESCRIPTION OF THE INVENTION

Figure 1:
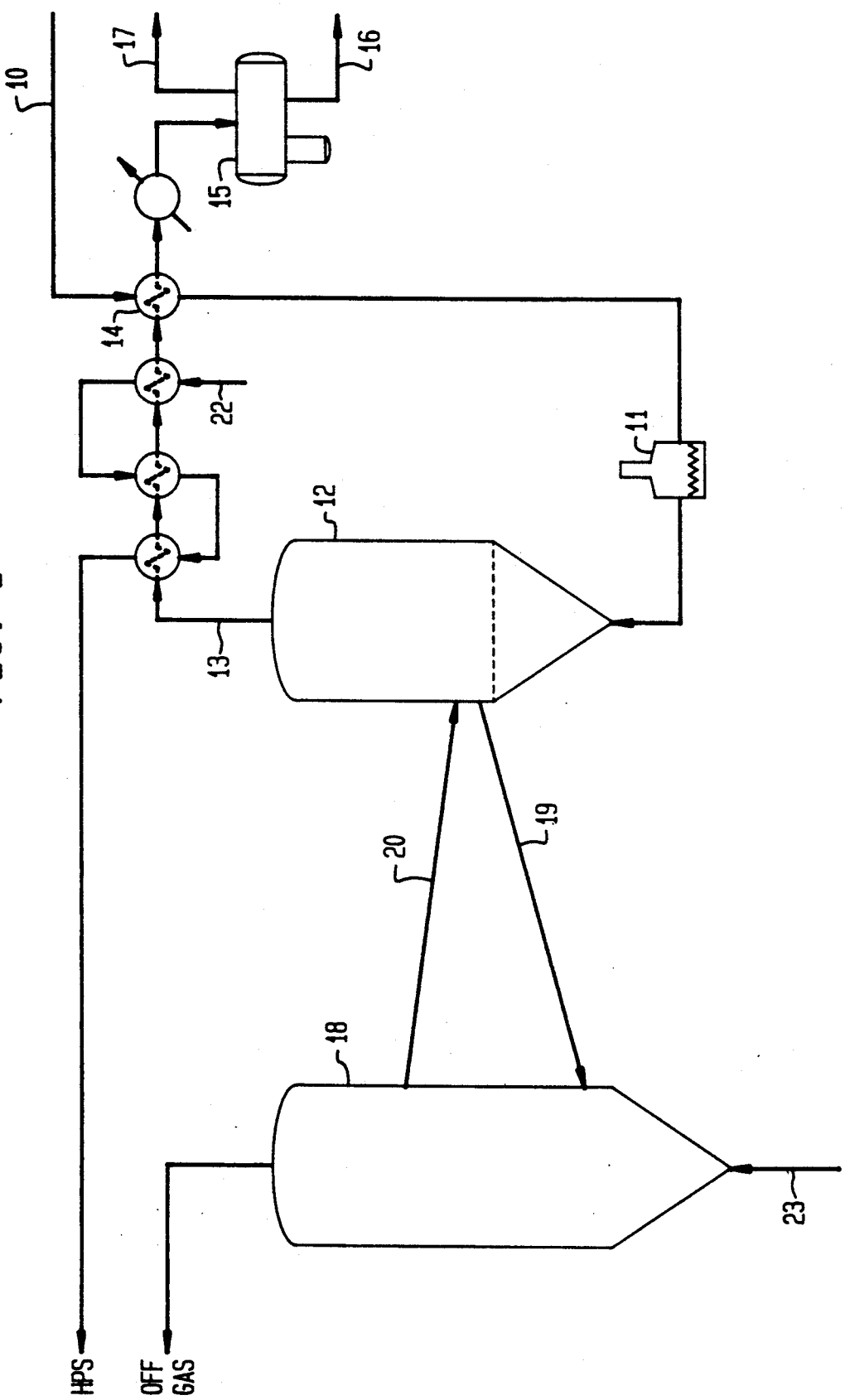
FIG. 1 is a schematic process flow diagram of Mobil Olefins to Gasoline (MOG) process.

In the preferred embodiment of the instant invention the principal components of known processes are integrated in a manner providing a highly advantageous and surprising advancement in refinery technology leading to the production of high octane gasoline. Known processes are combined in a unique configuration that provides enhancement of the performance of component processes as well as achieving surprising advantages for the integrated process. The processes integrated include etherification of tertiary olefins to produce methyl tertiary butyl ether (MTBE) and methyl tertiary amyl ether (TAME), the etherification of linear olefins and the conversion of olefins to higher molecular hydrocarbons such as gasoline, distillate and aromatics by processes known as the MOG process, MOGD and M-2 Forming. The above processes are further integrated in a novel way through a dehydrogenation step to yield the fully integrated process of the instant invention. These known processes are discussed further herein.

In the preferred embodiments of this invention lower alkanol such as methanol, ethanol or isopropanol is reacted with hydrocarbon feedstock containing mixed olefins in a serially integrated process to etherify both branched and linear olefins and produce high octane gasoline contain lower alkyl ethers of branched and linear olefins. The lower alkyl groups include methyl, ethyl and isopropyl. The olefins of particular interest are tertiary olefins such as iso-butylene and isoamylene to produce tertiary alkyl ethers, particularly methyl tertiary butyl ether (MTBE) and methyl tertiary amyl ether (TAME). $C_3-C_4$ linear olefins are converted to lower alkyl isopropyl ether and sec-butyl ether. Unreacted olefins and by-products from linear olefins etherification such as dimethyl ether and methanol are converted to higher molecular hydrocarbons boiling in the gasoline range. Preferred ethers from linear olefins are methyl isopropyl ether and methyl sec-butyl ether. In the first etherification reaction, methanol is generally present in an excess amount between 1 wt. % to 100 wt %, based upon converted tertiary olefins. Following a first etherification reaction, the etherification reaction effluent stream is separated to produce $C_5+$ gasoline rich in tertiary alkyl ethers and a hydrocarbon stream containing linear olefins for further etherification in a second etherification reaction. The composition of the first etherification effluent comprises unreacted alkanol, hydrocarbons including a major portion of $C_4+$ hydrocarbons containing unreacted linear olefins and lower alkyl tertiary alkyl ethers such as methyl tertiary alkyl ethers.

Methanol is the preferred lower alcohol used in the present invention. Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %. The etherification catalyst employed for tertiary olefin etherification is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites. Typical hydrocarbon feedstock materials for etherification reactions include olefinic streams, such as FCC light naphtha and butenes rich in iso-olefins. These aliphatic streams are produced in petroleum refineries by catalytic cracking of gas oil or the like.

The reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977. An article entitled "MTBE and TAME - A Good Octane Boosting Combo," by J. D. Chase, et al., *The Oil and Gas Journal*, Apr. 9, 1979, pp. 149–152, discusses the technology. A preferred catalyst is a bifunctional ion exchange resin which etherifies and isomerizes the reactant streams. A typical acid catalyst is Amberlyst 15 sulfonic acid resin.

MTBE and TAME are known to be high octane ethers. The article by J. D. Chase, et al., *Oil and Gas Journal*, Apr. 9, 1979, discusses the advantages one can achieve by using these materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

Processes for producing and recovering MTBE and other methyl tertiary alkyl ethers from $C_4$–$C_7$ isoolefins are known to those skilled in the art, such as disclosed in U.S. Pat. Nos. 4,544,776 (Osterburg, et al.) and 4,603,225 (Colaianne et al.). Various suitable extraction and distillation techniques are known for recovering ether and hydrocarbon streams from etherification effluent.

The process of this invention is based on the integration of the above tertiary olefin etherification with the known process that linear monoolefins, under the proper reaction conditions, react in the presence of an acid catalyst, preferably solid insoluble acid catalyst, with a low molecular weight primary or secondary monohydric alcohol to selectively produce ethers.

Linear monoolefins and mixtures thereof useful in the process of this invention include, broadly, those having 3 to 15 carbon atoms, and these have the structure $$R_1\text{---CH}=\text{CH---}R_2$$

wherein $R_1$ and $R_2$ individually are hydrogen or alkyl groups and the total carbon atoms in $R_1$ plus $R_2$ is from 1 to 13. However, in a preferred embodiment of the present invention, the preferred linear olefins are those having 3 to 5 carbon atoms, i.e. the total carbon atoms in $R_1$ plus $R_2$ is 1 to 3. Particularly preferred feed is propylene, 1-butene and 2-butene.

Although the hydrocarbon feed to the second etherification process may be substantially linear olefin (i.e. greater than 90 wt % of olefin), it is a feature of the invention that the reaction proceeds well in the presence of paraffins.

The alcohol to be reacted with the linear olefin is any primary or secondary alcohol having up to 4 carbon atoms. These include the primary alcohols methanol, ethanol, n-propanol, n-butanol and isobutanol; and the secondary alcohols isopropanol and sec-butanol. The lower alcohols are preferred, with methanol being particularly preferred.

It is generally advantageous, and therefore preferred, to conduct the process of this invention as a continuous operation. Since the linear olefin etherification reaction is exothermic, temperature control is facilitated by a continuous cascade operation with two or more reactors in sequence and with interstage cooling. Operable reaction conditions are given in Table I for linear olefin etherification. The weight hourly space velocity (WHSV) referred to in Table I and elsewhere herein, unless explicitly stated to be otherwise, is based on reactants, i.e. the total weight of linear olefin plus alcohol divided by the total weight of binder-free insoluble acid catalyst per hour. The corresponding contact times, of course, apply to batch conversions.

TABLE 1

| | Reaction Conditions | | | |
|---|---|---|---|---|
| | Mol Ratio alcohol/olefin | Temp. °C. | Press. atm. | WHSV $Hr^{-1}$ |
| Broad | 0.1–10 | 50–300 | 1.0–300 | 0.05–50 |
| Preferred | 0.3–3 | 80–250 | 5–200 | 0.2–20 |
| Most Preferred | 0.5–2 | 100–210 | 10–100 | 0.5–10 |

The principal ether product or products produced depends on the linear olefin and the alcohol charged. In the case of methanol and propylene, for example, the principal reaction product is methyl isopropyl ether. With butene-1 or the cis- or trans-butene-2, methyl sec-butyl ether is formed. In brief, the ethers formed are those predicted by the Markovnikov rule for addition to the double bond of the linear olefin. In the case of the higher molecular weight linear monoolefins, or mixtures of olefins, the principal reaction product is a mixture of such ethers.

The principal by-products formed in the etherification of linear olefins is the ether and water resulting from the autocondensation of the alcohol charged. Other by-products include alcohol resulting from the hydration of the linear monoolefin, and the ether formed by the self-condensation of the latter alcohol. Also formed is a small amount of hydrocarbon believed to be the oligomer of the olefin charged. This hydrocarbon by-product appears to account for less than 5 wt % of the total olefin converted under moderate temperatures, such as at a temperature not higher than about 160° C.

The new process of this invention for manufacturing ether-rich gasolines from refinery feedstock such as FCC naphtha utilizes a two stage etherification system including an interstage separation section. Unreacted olefins from the second etherification reaction are converted to higher molecular weight hydrocarbons such as gasoline in the MOG process as shown in FIG. 1. Optionally, the unreacted olefins may be converted to gasoline and distillate by the MOGD process or olefins and paraffins may be converted to aromatics by the M-2 Forming process. The first stage etherification preferably operates at a relatively low temperature (37°–93° C.) in order to efficiently convert tertiary olefins to high octane alkyl tertiary-alkyl ethers. The second etherification stage converts the first stage reactor unconverted tertiary C4–C5's, excess alcohol, and linear C5- olefins to alkyl tertiary-alkyl ethers and alkyl iso-alkyl ethers. The second stage operates at a higher temperature (preferably 50°–300° C.) The preferred catalysts include Amberlyst 15 in the first stage and zeolite Beta in the second stage. The first stage preferably consists of a single fixed bed reactor in which the extent of reaction is at least 65% of equilibrium.

The MOG process preferred in the present invention is well-known in the petroleum refining arts and provides a system for upgrading light olefins to liquid hydrocarbons, utilizing a continuous process for producing fuel products by oligomerizing olefinic components to produce higher hydrocarbon products for use as fuel or the like. The preferred MOG feedstock contains $C_2$-$C_4$ alkenes (mono-olefin) in the range of about 10 to 90 wt %. Non-deleterious components, such as methane and other paraffins and inert gases, may be present. A particularly useful feedstock is a light gas by-product of FCC gas oil cracking units containing typically 10-40 mol % $C_2$-$C_4$ olefins and 5-35 mol % $H_2$ with varying amounts of $C_1$-$C_3$ paraffins and inert gas, such as $N_2$. The process may be tolerant of a wide range of lower alkanes, from 0 to 90%.

Conversion of lower olefins, especially ethene, propene and butenes, over HZSM-5 is effective at moderately elevated temperatures and pressures. Operating details for typical olefin oligomerization units are disclosed in U.S. Pat. Nos. 4,456,779; 4,497,968 (Owen et al.) and 4,433,185 (Tabak), incorporated herein by reference. The conversion of paraffins and/or olefins to aromatics, i.e. M-2 Forming, is described in U.S. Pat. Nos. 3,760,024 and 3,756,942 to Cattanach, U.S. Pat. No. 3,845,150 to Yan et al., U.S. Pat. No. 4,090,949 to Owen et al. These patents are also incorporated herein by reference in their entirety.

Catalysts useful in the MOG process and the process of the instant invention include a unique group of metallosilicate zeolites. Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalyst preferred for use in olefins conversion and the process of the present invention includes the medium pore (i.e., about 5-7 angstroms) shape selective crystalline aluminosilicate zeolites having a silica to alumina ratio of about 20:1 or greater, a constraint index of about 1-12, and acid cracking activity (alpha value) of about 2-200. Representative of the shape selective zeolites are ZSM-5, ZSM-11, ZSM-12, ZSM-22, ZSM-23, ZSM-35, ZSM-38, and ZSM-48. ZSM-5 is disclosed in U.S. Pat. No. 3,702,886 and U.S. Pat. Re. No. 29,948. Other suitable zeolites are disclosed in U.S. Pat. Nos. 3,709,979 (ZSM-11); 3,832,449 (ZSM-12); 4,076,979; 4,076,842 (ZSM-23); 4,016,245 (ZSM-35); and 4,375,573 (ZSM-48). The disclosures of these patents are incorporated herein by reference.

In FIG. 1, a schematic process flow diagram of Mobil Olefins to Gasoline (MOG) process is presented. An olefins rich feedstock 10 is preheated in heater 11 and passed to MOG reactor 12 containing a fluidized bed of acidic, shape selective metallosilicate catalyst, preferably ZSM-5. The catalyst may have an acid cracking value of about 2 to 35, preferably about 2-5. The feedstock is preheated to a temperature of 65°-175° C. and the reactor operating conditions comprise temperatures of about 215°-535° C. and pressures of about 50-2000 kPa and a weight hourly space velocity (WHSV) based on active catalyst of about 0.5-10. The reactor effluent 13 is cooled, optionally in indirect heat exchange with feedstock 14 and cooling water 22 and separated in separator 15 to produce unstabilized liquid $C_5+$ gasoline 16 and vapor product 17. Spent catalyst is passed to regenerator vessel 18 via line 19 for oxidative regeneration with air 23 and regenerated catalyst is recycled to reactor 12 through line 20. Under these conditions greater than 80% of the lower olefins in the feedstock are converted to higher hydrocarbons.

In one embodiment of the present integrated invention unreacted paraffins from the effluent of the MOG process are passed to a dehydrogenation zone where they are converted to olefins. The $C_4$ olefin fraction from dehydrogenation is then recycled to the first etherification zone of the integrated process for conversion to ethers. It has been established that the conversion of paraffins, such as propane and butane, to mono-olefins, such as propylene and butylene, can be accomplished by thermal or catalytic dehydrogenation. A general discussion of thermal dehydrogenation (i.e., steam cracking) is presented in *Encyclopedia of Chemical Technology*, Ed. by Kirk and Othmer, Vol. 19, 1982, Third Ed., pp. 232-235. Various processes for catalytic dehydrogenation are available in the prior art. These processes include the Houdry Catofin process of Air Products and Chemical, Inc., Allentown, Pa., the Oleflex process of UOP, Inc., Des Plaines, Ill. and a process disclosed by U.S. Pat. No. 4,191,846 to Farha, Jr. et al. The Houdry Catofin process, described in a magazine article, "Dehydrogenation Links LPG to More Octanes", Gussow et al, *Oil and Gas Journal*, Dec. 8, 1980, involves a fixed bed, multi-reactor catalytic process for conversion of paraffins to olefins. Typically, the process runs at low pressures of 5-30 inches of mercury absolute, and high temperatures with hot reactor effluent at 550°-650° C. Dehydrogenation is an endothermic reaction, so it normally requires a furnace to provide heat to a feed stream prior to feeding the feed stream into the reactors. The UOP Oleflex process, disclosed in an article "$C_2/C_5$ Dehydrogenation Updated", Verrow et al, *Hydrocarbon Processing*, April 1982, used stacked catalytic reactors. U.S. Pat. No. 4,191,846 to Farha, Jr. et al teaches the use of group VIII metal containing catalysts to promote catalytic dehydrogenation of paraffins to olefins.

Figure 2:
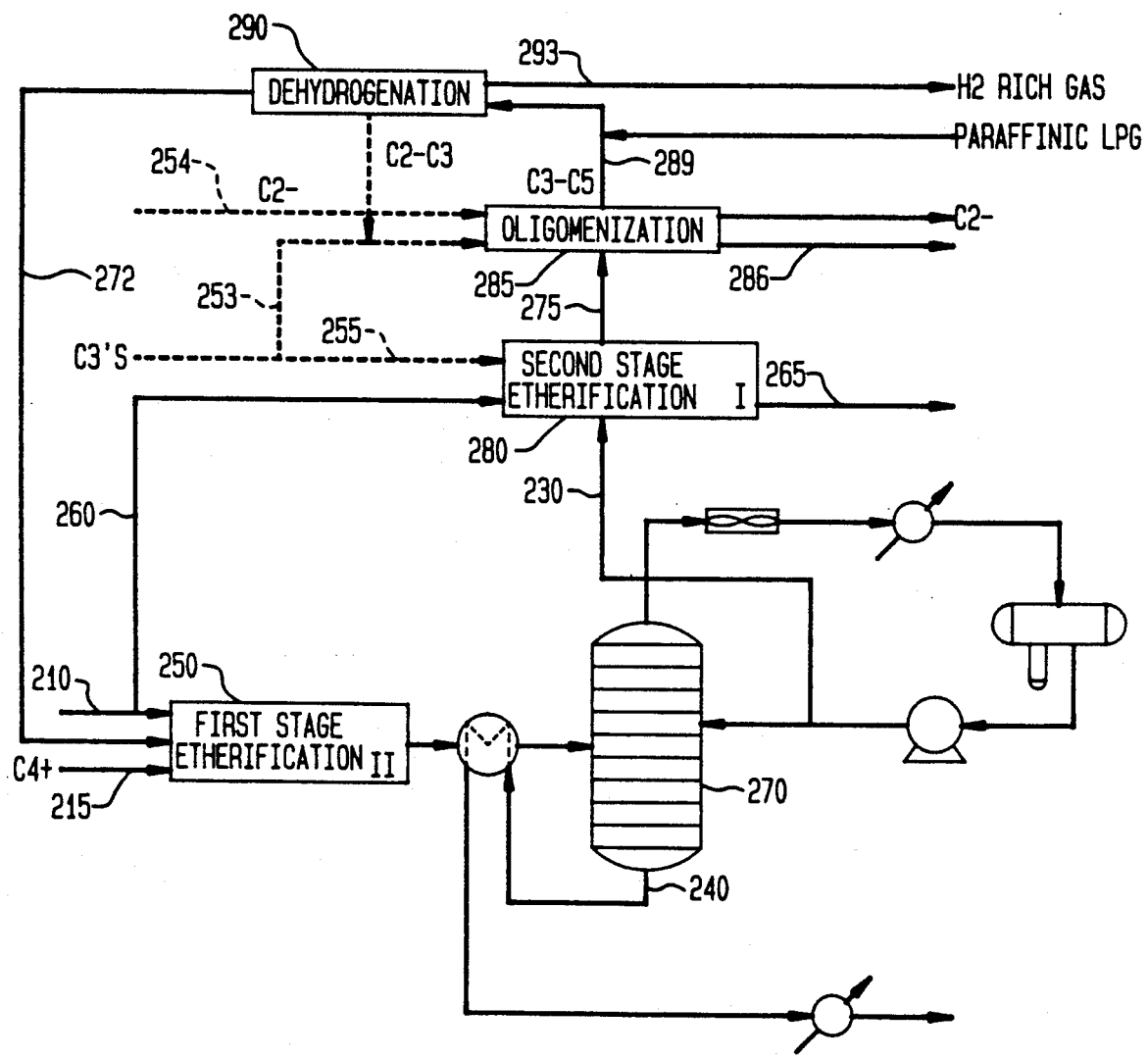
FIG. 2 is a schematic drawing of a preferred embodiment of the present invention.

Referring now to FIG. 2, the integrated process of the present invention is illustrated in a flow schematic. Methanol and hydrocarbon reactants are passed to the first etherification reactor 250 in conduits 210 and 215. Preferably the hydrocarbon feed is rich in isoalkenes and also contains other paraffinic and linear olefinic hydrocarbons. By virtue of the discovery embodied in the instant invention, the quantity of methanol passed to the etherification unit can be between 1 and 100 percent in excess of the reacted isoalkenes in an etherification reaction. Etherification is conducted as described heretofore and the etherification product is passed as an effluent stream to separator 270. Methanol is separated overhead preferably as an azeotropic mixture with $C_5-$ paraffinic and olefinic hydrocarbons which are passed 230 to a second etherification zone 280. A bottom fraction is withdrawn from separator 270 through conduit 240 which contains methyl tertiary alkyl ethers, such as MTBE and TAME, in admixture with $C_5+$ gasoline. The gasoline separated exhibits a high motor octane value and high research octane value. In the second etherification zone 280 linear olefins are converted to methyl ethers, optionally with added methanol from conduit 260 or $C_3$ hydrocarbons through conduit 255. Product $C_5+$ gasoline rich in ethers is separated through conduit 265 while byproducts, including dimethly ether (DME) and methanol, and uncoverted $C_4-$ hydrocarbons are passed through conduit 275 to MOG unit 285. Optionally, FCC $C_3$'s and ethene are introduced into the MOG unit as feedstock through, respectively, conduits 253 and 254. In the MOG unit olefins are converted to $C_5+$ gasoline under condition described herein before. The product gasoline is recovered through conduit 286. Unreacted $C_3-C_5$ paraffins separated from the MOG unit are passed 289 to dehydrogenation unit 290, optionally with added LPG paraffinic feed. $C_4$ olefins are separated from the dehydrogenation reactor effluent and passed 292 to the first etherification stage for further etherification in conjunction with fresh hydrocarbon feedstock. By-product hydrogen-rich gas is recovered 293 from the dehydrogenation unit.

Although the present invention has been described with preferred embodiments and examples, it is to be understood that modifications and variations may be resorted to without departing from the spirit and scope of this invention, as those skilled in the art will readily understand. Such modifications and variations are considered to be within the purview and scope of the appended claims.

What is claimed is:

1. An integrated process for the production of ether-rich rich liquid fuels, comprising:
   (a) contacting a fresh mixture of lower alkanol and a light hydrocarbon feedstock containing linear olefins and $C_4+$ tertiary olefins with an acidic etherification catalyst in a first etherification zone under tertiary olefin etherification conditions whereby an etherification effluent stream containing lower alkyl tertiary alkyl ethers is produced;
   (b) separating said etherification effluent stream to provide a first stream comprising ether-rich $C_5+$ gasoline and a second stream comprising unreacted lower alkanol and linear olefins of $C_5-$ hydrocarbons;
   (c) contacting said second stream with an acidic catalyst in a second etherification zone under conditions effective to etherify said linear olefinic hydrocarbons;
   (d) recovering a first stream comprising $C_5+$ gasoline containing lower alkyl ethers of said $C_5-$ linear olefins and a second stream comprising unreacted olefins of $C_4-$ hydrocarbons from said second etherification zone;
   (e) passing said second stream to an olefins to higher molecular weight hydrocarbons conversion zone in contact with an acidic metallosilicate catalyst under olefins and oxygenates conversion conditions at elevated temperature whereby higher molecular $C_5+$ gasoline boiling range hydrocarbons are produced plus $C_5-$ paraffinic hydrocarbon by-product.

2. The process of claim 1 including the step of introducing a fresh stream of said alkanol to step (c) etherification zone.

3. The process of claim 1 including the further step of introducing a fresh stream of $C_3$ hydrocarbons to step (c) etherification zone and step (e) conversion zone.

4. The process of claim 1 wherein step (a) etherification conditions comprise a high excess of said alkanol over $C_4+$ tertiary olefins whereby the etherification reaction equilibrium is shifted substantially toward the formation of $C_5+$ ethers.

5. The process of claim 4 wherein said excess of said alkanol is between about 3 and 100 percent.

6. The process of claim 4 wherein said excess of alkanol is about 10 percent.

7. The process of claim 1 wherein said tertiary alkyl ethers comprise MTBE and TAME.

8. The process of claim 1 wherein step (c) catalyst comprises a shape-selective, acid aluminosilicate zeolite-type catalyst having the structure of zeolite Beta.

9. The process of claim 1 wherein step (c) etherified linear olefins comprise methyl isopropyl ether and methyl sec-butyl ether.

10. The process of claim 1 wherein said first zone etherification conditions comprise temperature between 37° and 93° C. and said second zone conditions comprise temperature between 50° and 300° C.

11. The process of claim 1 including the further steps of:
   passing the $C_3-C_5$ fraction of step (e) $C_5-$ paraffinic hydrocarbon by-product to a dehydrogenation zone under paraffins dehydrogenation conditions whereby olefins are produced and hydrogen rich fuel gas; and
   passing said olefins to step (a) etherification zone in conjunction with said light hydrocarbon feedstock.

12. The process of claim 1 wherien said metallosilicate comprises zeolite ZSM-5.

13. The process of claim 1 including the further step of introducing ethene rich fuel gas as feedstock to step (e) conversion zone.

14. In the process for the production of methyl tertiary alkyl ethers comprising reacting a mixture comprising methanol and $C_4+$ hydrocarbons containing tertiary and linear olefins in contact with acid etherification catalyst under etherification conditions in an isoolefins etherification zone to produce a product stream comprising $C_5+$ methyl tertiary alkyl ethers, unreacted methanol and $C_5-$ hydrocarbons containing linear olefins; separating said product stream into unreacted methanol, unreacted $C_5-$ hydrocarbons and $C_5+$ ethers, recycling unreacted methanol and recovering a hydrocarbon stream rich in $C_5+$ methyl tertiary alkyl ethers, the improvement comprising:
   (a) contacting said $C_5-$ hydrocarbons with an acidic catalyst in a linear olefins etherification zone under conditions effective to etherify linear olefinic fraction of said hydrocarbons;
   (b) recovering a first stream comprising $C_5+$ gasoline containing methyl ethers of said $C_5-$ hydrocarbons and a second stream comprising unreacted olefins of $C_5-$ hydrocarbons, methanol and dimethyl ether from said linear olefins etherification zone;
   (c) passing said second stream to an olefins to gasoline conversion zone in contact with an acidic metallosilicate catalyst under olefins and oxygenates conversion conditions at elevated temperature whereby $C_5+$ gasoline is produce dplus $C_5-$ paraffinic hydrocarbon by-product.

15. The process of claim 14 including the further steps of:
passing the $C_3$–$C_5$ fraction of said $C_5-$ paraffinic hydrocarbon by-product to a dehydrogenation zone under paraffins dehydrogenation conditions whereby olefins are produced and hydrogen rich fuel gas; and
passing said olefins to said isoolefins etherification zone in conjunction with said light hydrocarbon feedstock.

16. The process of claim 14 including the step of introducing a fresh stream of methanol to said linear olefins etherification zone.

17. The process of claim 14 including the further step of introducing a fresh stream of $C_3$ hydrocarbons to said linear olefins etherification zone and step (c) conversion zone.

18. The process of claim 14 wherein isoolefins etherification conditions comprise temperature between 37° and 93° C. and linear olefins etherification conditions comprise temperature between 50° and 300° C.

19. The process of claim 1 wherein said lower alkanol is taken from the group comprising essentially methanol, ethanol and isopropanol.

20. The process of claim 1 wherein said olefins conversion conditions comprise olefin to gasoline conversion conditions and said higher molecular weight hydrocarbons comprise gasoline boiling range hydrocarbons.

21. The process of claim 1 wherein said olefins conversion conditions comprise olefin to gasoline and distillate conversion conditions and said higher molecular weight hydrocarbons comprise gasloine and distillate boiling range hydrocarbons.

22. The process of claim 1 wherein said olefins conversion conditions comprise olefin and paraffin conversion conditions and said higher molecular weight hydrocarbons comprise aromatics.

* * * * *